United States Patent [19]

Newgard et al.

[11] Patent Number: 5,064,416
[45] Date of Patent: Nov. 12, 1991

[54] SELF-OCCLUDING INTRAVASCULAR CANNULA ASSEMBLY

[76] Inventors: Kent W. Newgard, 1931 Beverly Glen Dr., Santa Ana, Calif. 92705; Mark G. Gordon, 13591 Malena Dr., Tustin, Calif. 92680

[21] Appl. No.: 381,760

[22] Filed: Jul. 17, 1989

Related U.S. Application Data

[63] Continuation-in-part of Ser. No. 199,118, May 26, 1988, Pat. No. 4,874,377.

[51] Int. Cl.$^5$ ............................................. A61M 5/178
[52] U.S. Cl. ..................................... 604/167; 604/256; 251/149.1
[58] Field of Search ................ 604/237, 167, 236, 256, 604/247; 251/149.1

[56] References Cited

U.S. PATENT DOCUMENTS

| | | |
|---|---|---|
| 2,682,874 | 7/1954 | Hickey . |
| 2,707,953 | 5/1955 | Ryan . |
| 3,084,688 | 4/1963 | McConnaughey ................ 604/237 |
| 3,091,240 | 5/1963 | McConnaughey et al. ........ 604/237 |
| 3,620,500 | 11/1971 | Santomieri . |
| 3,834,380 | 9/1974 | Boyd . |
| 3,856,010 | 12/1974 | Moorehead et al. . |
| 3,856,020 | 12/1974 | Kovac . |
| 3,875,938 | 4/1975 | Mellor . |
| 4,006,744 | 2/1977 | Steer . |
| 4,143,858 | 3/1979 | Abramson . |
| 4,177,809 | 12/1979 | Moorehead . |
| 4,192,304 | 3/1980 | Millet . |
| 4,387,879 | 6/1983 | Tauschinski . |
| 4,392,856 | 7/1983 | Lichtenstein . |
| 4,445,893 | 5/1984 | Bodicky . |
| 4,512,766 | 4/1985 | Vailancourt . |
| 4,683,916 | 8/1987 | Raines . |
| 4,874,377 | 10/1989 | Newgard et al. ................... 604/167 |

OTHER PUBLICATIONS

Brochure entitled "Percutaneous Valvuloplasty Catheter Accessories" by Cook Inc. (1987).

Primary Examiner—Robert Bahr
Assistant Examiner—Linda Dvorak
Attorney, Agent, or Firm—Stetina and Brunda

[57] ABSTRACT

A self-occluding cannula assembly comprising a generally tubular cannula sheath having a connecting hub formed on one end thereof and including an occluding means positioned within the inner bore of said connecting hub. The occluding means comprises (a) a generally frusto conical dilator projection; (b) an elastomeric valving member positioned transversely within the bore of the connecting hub proximal to said dilator projection. The elastomeric valving member is peripherally axially compressed so as to cause displacement, distortion and/or rheological flowing of the elastomeric material thereof in a radially inward direction. An elastically openable and closable aperture is formed in the mid-portion of the valving member and the valving member is alternately movable between an "occluding" position wherein the aperture is closed so as to prevent fluid flow through the cannula and a "non-occluding" position wherein the aperture is open to allow fluid flow through the cannula.

11 Claims, 2 Drawing Sheets

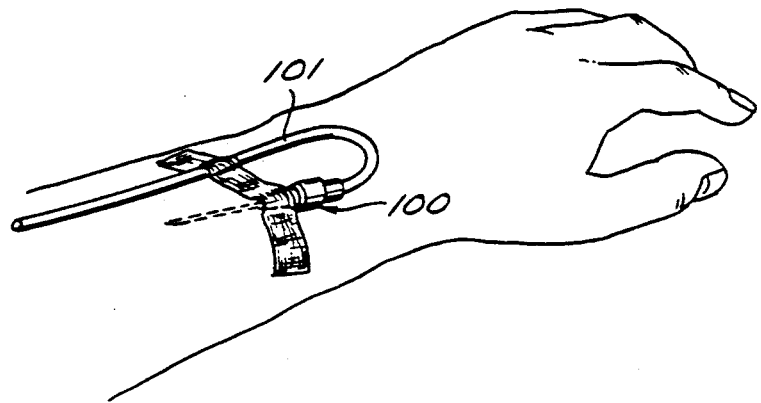
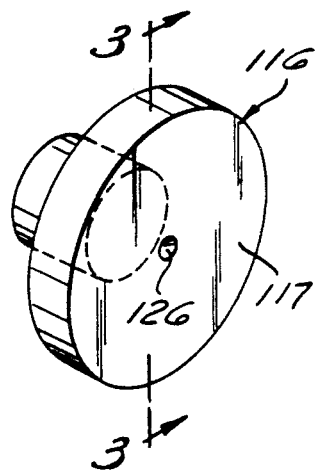
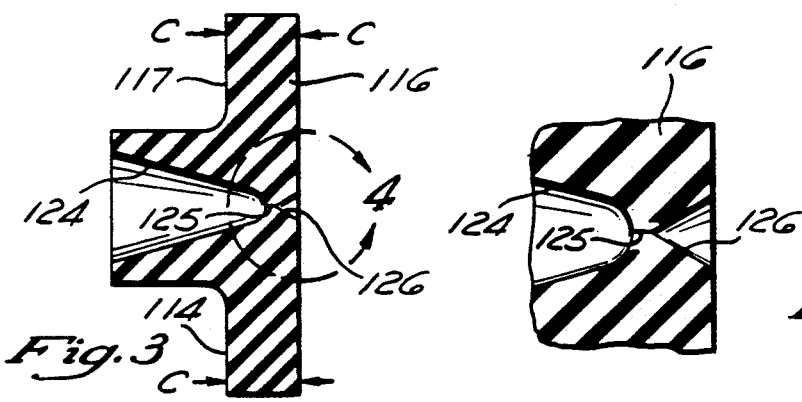
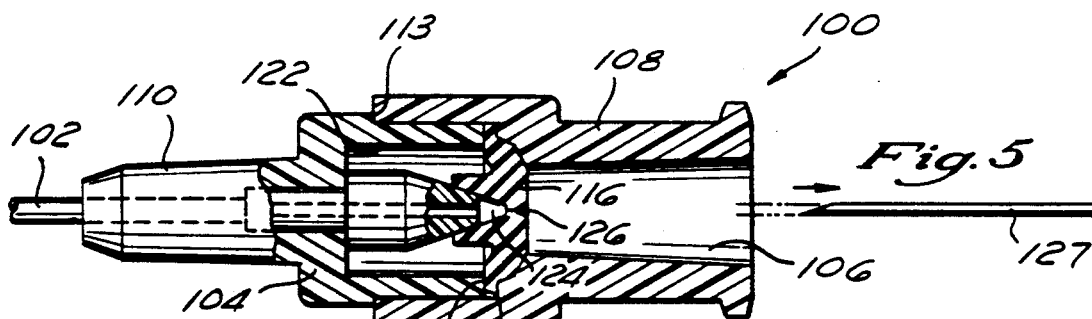
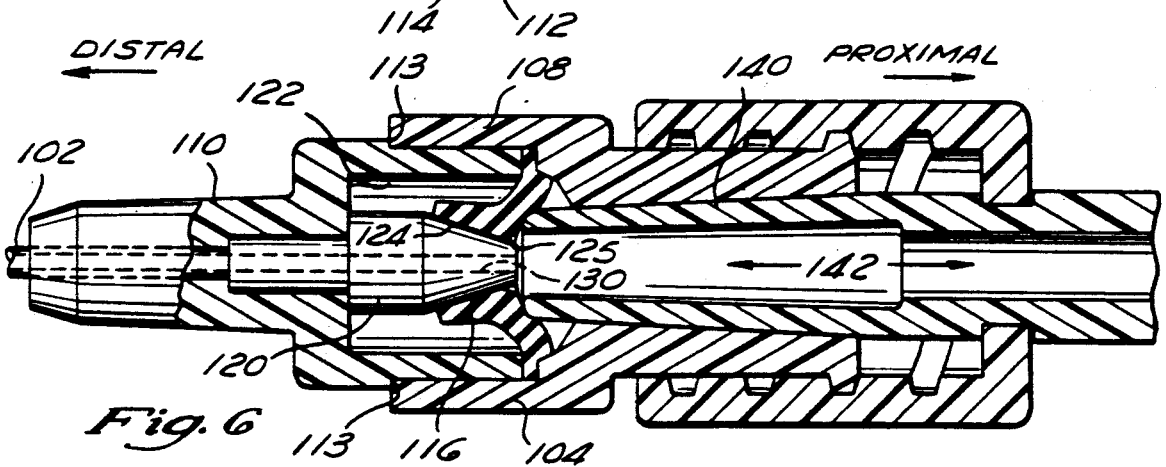

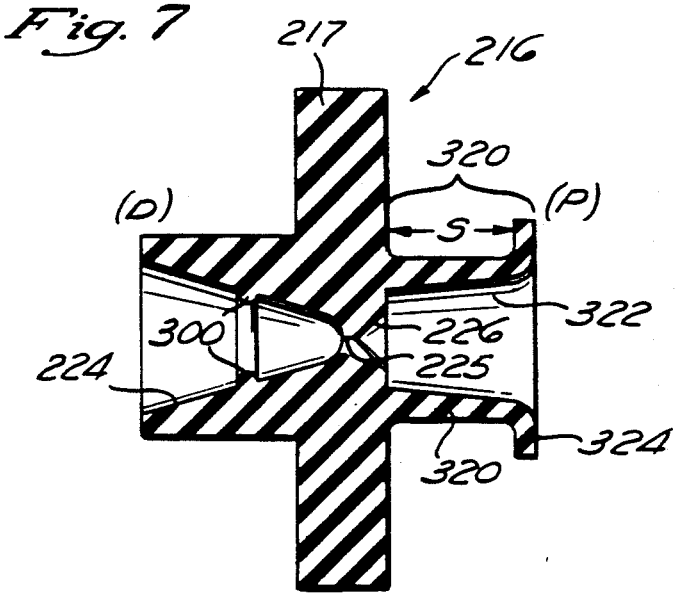
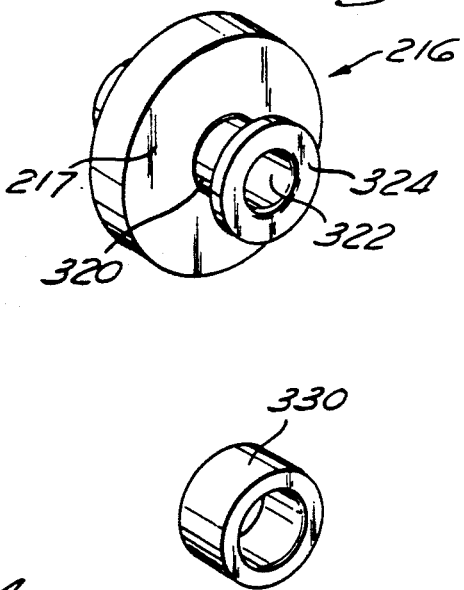
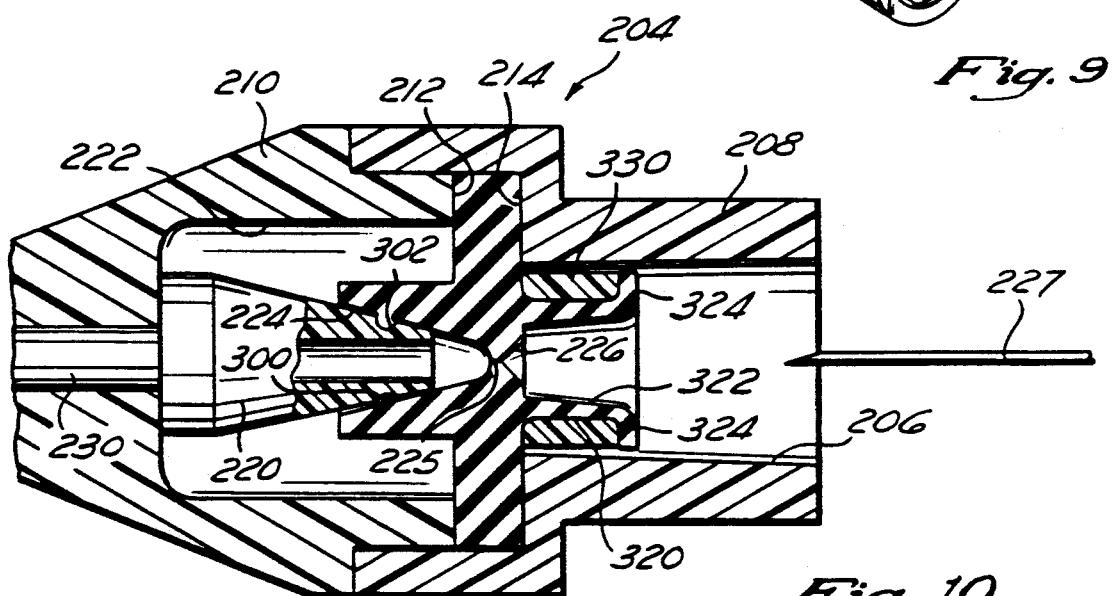
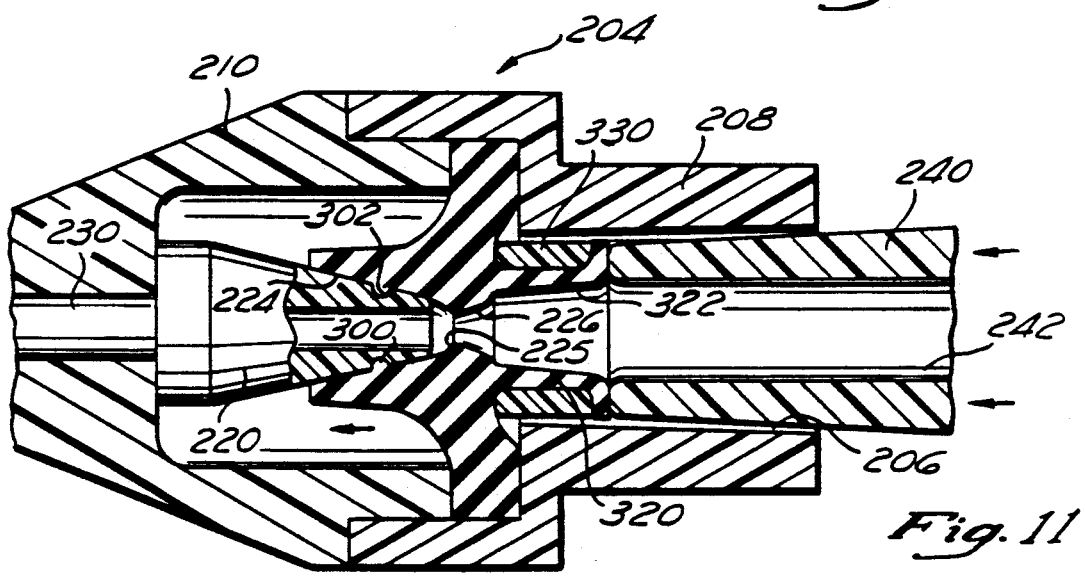

SELF-OCCLUDING INTRAVASCULAR CANNULA ASSEMBLY

RELATED INVENTIONS

This application is a continuation-in-part of patent application Ser. No. 199,118 filed on May 26, 1988, entitled Self-occluding Intravascular Cannula Assembly, now U.S. Pat. No. 4,874,377.

INCORPORATION BY REFERENCE

The entire disclosure of applicant's copending U.S. patent application Ser. No. 199,118, filed May 26, 1988, is incorporated herein by reference.

BACKGROUND OF THE INVENTION

This application pertains generally to the medical arts and more particularly to an improved self-occluding cannula assembly for insertion into blood vessels or various body cavities.

The invention is particularly applicable to flexible intravascular cannula of the type commonly used to administer intravenous infusions and/or to monitor pressures within arteries and/or veins of the human body. Accordingly, the invention will be described with particular reference to such applications. It must be appreciated, however, that the invention has utility in numerous other applications wherein it is desirable to prevent or limit back flow of bodily fluids from a tubular cannula. Examples of other types of cannula wherein the present invention may be utilized include, but are certainly not limited to; trocars for intra-abdominal or intra-thoracic insertion; long flexible catheters used for monitoring central venous pressures and for centrally administering drugs and various infusates; and various indwelling semi-permanent catheters such as the type commonly used in the administration of total parenteral alimentation.

Although many of the cannula in which the invention will be used may incorporate removable introducer needles or stylets to effectuate puncture of soft tissues, it must be further appreciated that the utility of the invention is not limited to such needle-bearing devices. In fact, the occluding means of the present invention may be employed with even the simplest types of medical tubing to prevent back flow of fluids therefrom.

It is common medical practice to insert tubular cannula into blood vessels for the infusion of various fluids and/or the monitoring of intravascular pressures. A basic intravenous cannula assembly of the prior art comprises a flexible cannula sheath having a rigid introducer needle positioned axially therewithin. The beveled tip of the hollow introducer needle extends a short distance beyond the distal tip of the cannula to permit easy penetration of the skin and underlying tissues. When the needle tip enters the target blood vessel, blood immediately fills the lumen of the needle and advances proximally to a transparent receptical on the needle hub where it may be readily viewed. Alternatively the needle hub may be connected to a syringe wherein a small amount of the blood may be visibly withdrawn into an existing quantity of saline solution. Thereafter the introducer needle is withdrawn. Thus, the cannula sheath remains in place as a means for subsequent infusion of intravenous fluids and/or monitoring of intravascular pressures.

Because the flexible cannula sheath comprises a generally hollow tube, blood will rapidly back flow (i.e. flash back) through the inner lumen of the cannula upon withdrawal of the introducer needle. As a result, a certain amount of blood invariably flows out of the proximal end of the cannula immediately after withdrawal of the introducer needle. Regardless of how adept the user may be at attaching an appropriate solution administration line or other auxiliary tube to the proximal end of the cannula, a certain amount of blood loss is likely to occur.

Likewise, if the attendant solution administration line or other tube subsequently becomes disconnected from the cannula, blood will immediately back flow from the cannula and may continue to flow therefrom until the disconnected line has been discovered and reconnected.

Indeed, any unnecessary back flow of blood from the cannula lumen is undesirable from a standpoint of general hygiene as well as in view of the present potential for blood born disease transmission Serious diseases such as Hepatitis and Acquired Immune Deficiency Syndrome are known to be transmissible to health care workers and others through contact with infectious blood.

A number of valving apparatus have been disclosed for selectively closing off and/or preventing back flow from intravenous cannula Many such valving apparatus comprise exteriorly mounted clamps, clips, compressors and other devices adapted to pinch off or otherwise prevent back flow from a catheter Additionally, a number of self-actuating or automatic valving members have been disclosed. Such self-actuating or automatic valving members are generally positioned within the bore of a cannula hub and purportedly function to prevent inadvertent back flow therefrom. Examples of self-actuating and/or automatic valving members of the prior art include those described in U.S. Pat. No. 3,620,500 (Santomieri), U.S. Pat. No. 4,143,853 (Abramson), U.S. Pat. No. 4,387,879 (Tauschinski), U.S. Pat. No. 4,512,766 (Vailancourt) and U.S. Pat. No. 4,683,916 (Raines).

Although the invention described in U.S. patent application Ser. No. 199,118 constitutes a significant advancement over the prior art, it has been found that certain embodiments of the elastic "obturator" member incorporated therein may be prone to inadvertent deformation whereby a portion of the obturator member may collapse into the proximal lumen of the frusto conical dilator projection during the movement of the obturator member from its initial "occluding" configuration to its "nonoccluding" configuration Such inadvertent deformation or collapse of the obturator member operates to obstruct the cannula lumen and interferes with normal operability of the cannula.

Accordingly, there has been identified a need in the art for further modifications and/or improvements of the self-occluding intravascular cannula assembly described in U.S. patent application Ser. No. 199,118.

SUMMARY OF THE INVENTION

In accordance with the present invention, there is provided an improved self-occluding cannula assembly which generally comprises a pliable cannula sheath having an introducer needle retractably axially disposed therewithin. The introducer needle is initially positioned such that the beveled tip of the needle extends slightly beyond the distal tip of the cannula sheath to facilitate percutaneous insertion of a distal portion of the sheath into a blood vessel or the like.

A connecting hub is formed on the proximal end of the cannula sheath to facilitate connection of the cannula to an attendant solution administration tube, syringe, monitoring line or the like.

Occluding means are formed within the cannula hub. Such occluding means comprise (a) a conical or frusto conical dilator projection; and (b) a peripherally compressed, elastomeric valving member having an elastically openable and closable aperture formed therein. The valving member is generally disc-shaped, cylindrical or otherwised configured to fit transversely within the bore of the cannula hub, just proximal to the dilator projection. The periphery of the valving member is axially pinched or compressed between compression members or shoulders formed around the inner bore of the cannula hub. Such axial compression around the periphery of the elastic member causes the material of the valving member to undergo rheological flow and/or to exert pressure inwardly toward the mid-portion thereof. Such inward deformation, compression or flow of the valving member material causes substantial compressive force to be exerted from the compressed periphery of the valving member toward the mid-portion thereof.

Because the peripherally compressed elastomeric valving member is mounted transversely within the inner bore of the cannula hub, just distal to the dilator projection, any distally directed pressure (e.g. insertion of a male tubing connector or other object) may serve to advance or push the mid-portion of the valving member in a distal direction, causing the valving member to interact with the dilator projection. When the valving member has been advanced fully onto the dilator projection, the dilator projection will exert sufficient dilating pressure thereagainst to cause the elastically openable and closable aperture to assume an open position. With the valving member disposed over the dilator projection, and the openable and closable aperture in its fully "open" configuration, fluid will be permitted to flow through the lumen of the cannula without interference from the valving member.

The material of the valving member is sufficiently elastic and/or resilient that, upon removal of the tubing connector or other pressure exerting object, the valving member will resiliently retract from its advanced position over the frusto conical dilator projections thereby returning to its original nonoccluding position.

The return of the valving member to its nonoccluding position from its occluding position is facilitated by the specific configurations of the valving member and the dilator projection. In a preferred embodiment, the angular outer surface of the frusto conical portion of the dilator projection is relatively smooth and devoid of any ridges or course areas which could impede the desired slippage of the valving member therefrom.

Also, a conical notch, substantially analogous in configuration to the dilator projection, is formed in the body of the valving member with the elastically openable and closable aperture being formed at the apex of said conical notch. In its initial, or "nonoccluding" position, the valving member is positioned so that the dilator projection is no more than partially inserted into the conical notch so that no effective dilating or aperture-opening pressure is exerted thereby. When, however the distally directed pressure is applied to the valving member, it will advance over the dilator projection such that the dilator projection becomes disposed or thrust further into the conical notch, thereby exerting pressure about the aperture, causing dilation or opening thereof. Because the interior of the conical notch is analogous in shape to the frusto conical exterior of the dilator projection, the valving member will, upon removal of the distally directed pressure, automatically slip or retract back to its initial occluding position.

The radial compression stressing or rheological flow of material created by axial compression about the periphery of the valving member serves to bias or prestress the valving member to prevent undesirable buckling and/or lapse of any portion of the valving member into the proximal opening of the dilator projection. Such radial compression, stressing and/or rheological flow of the valving member material may further serve to enhance the desired, resilient and/or elastic self-closure of the valving member aperture when the valving member has moved from its "nonoccluding" position to its "occluding" position.

Additionally, the radial compression, stressing or inward rheological flowing of the elastomeric material of the valving member serves to hold the valving member in firm contact with the surface of the dilator projection so as to prevent leakage of blood or other fluids into the surrounding spaces. A substantially fluid tight seal is maintained between the valving member and the dilator projection is maintained regardless of whether the valving member is in its "occluding" or "nonoccluding" position.

These and other objects and advantages of the present invention will become apparent to those skilled in the art upon reading the following detailed description and consideration of the accompanying drawings.

BRIEF DESCRIPTION OF THE DRAWINGS

FIG. 1 is a perspective view of a first preferred intravascular cannula assembly of the present invention operatively disposed within a blood vessel and having a separate infusion line fluidly connected thereto;

FIG. 2 is a perspective view of a first elastomeric valving member which forms a component of a first preferred intravascular cannula assembly of the present invention;

FIG. 3 is a sectional view through line 3—3 of FIG. 2;

FIG. 4 is an enlarged view of region 4 of FIG. 3;

FIG. 5 is a longitudinal sectional view of a portion of a first preferred intravascular cannula assembly of the present invention;

FIG. 6 is a longitudinal sectional view of a portion of a first preferred intravascular cannula assembly of the present invention having a male tubing connector operatively inserted thereinto.

FIG. 7 is a longitudinal sectional view of a second elastomeric valving member which forms a component of a second preferred intravascular cannula assembly of the present invention;

FIG. 8 is a perspective view of a second elastomeric valving member which forms a component of a second preferred intravascular cannula assembly of the present invention;

FIG. 9 is a perspective view of a preferred rigid ring which is operatively positionable about the proximal extension of the second preferred elastomeric valving member shown in FIG. 8;

FIG. 10 is a longitudinal sectional view of a portion of a second preferred intravascular cannula assembly of the present invention;

FIG. 11 is a longitudinal sectional view of a portion of the second preferred intravascular cannula assembly of the present invention having a male tubing connector operatively inserted thereinto.

DETAILED DESCRIPTIONS OF PREFERRED EMBODIMENTS

A FIRST EMBODIMENT—FIGS. 1–6

The following detailed descriptions the accompanying drawings are provided for purposes of illustrating a presently preferred embodiment of the invention and are not intended to limit the scope of the invention in any way.

As shown in FIGS. 1–6, a first preferred self-occluding cannula assembly 100 of the present invention comprises a flexible cannula sheath 102 having a distal end and a proximal end. A cannula hub 104 is attached to the proximal end of tubular sheath 102. The cannula hub 104 comprises a female Leur type connector having an axial inner bore 106 formed therein. The cannula hub 104 is constructed of a proximal hub segment 108 and a distal hub segment 110. Distal hub segment 110 is slidably advancable into proximal hub segment 108 and subsequently affixed in position such that the proximal rim 112 of the distal hub segment 110 is in direct opposition to an annular shoulder 114 formed about the inner surface of the proximal hub segment 108. By such arrangement, the proximal rim 112 of the distal hub segment 110 and the annular shoulder 114 of the proximal hub segment 108 form opposing, compression exerting surfaces between which the peripheral flange 117 of valving member 116 may be axially pinched or compressed.

The compression of the peripheral flange 117 between the proximal rim 112 of distal segment 110 and the annular shoulder 114 of proximal segment 108 is carried out with sufficient force to cause an approximate five to thirty percent preferably twenty percent axial compression of the elastomeric material of the valving member 116 adjacent the peripheral flange 117 (i.e. the axial thickness of the peripheral flange is reduced approximately five to twenty percent from its normal uncompressed thickness. Such axial compression exerted about the peripheral flange 117 causes rheological flow, deformation and/or compressive forces to be formed in the valving member 116 which are directed from the periphery of the valving member 116 radially inward toward the center thereof Such radial forces have been found to reduce improper buckling of the valving member 116 during use.

A dilator projection 120 is formed or positioned within the inner bore 106 of the hub 104. Such dilator projection is firmly affixed to the distal portion 110 of hub 108 such that the body of the dilator projection 120 extends axially in a proximal direction within the center of bore 106. The dilator projection 120 is of frusto conical configuration and is sized and positioned such that an annular space 122 exists therearound within the inner bore 106 of the hub 108.

The dilator projection 120 and the valving member 116 are relatively sized, configured and positioned within the bore 106 of the cannula assembly 100 such that the dilator projection 120 is distal to and constantly in at least minimal abutment with the valving member 116, as shown.

The valving member 116 is provided with a major conical notch 124 formed in the distal side of the mid-region thereof and a minor conical notch 126 formed in the proximal side of the mid-portion thereof. A pinhole or substantially self sealing aperture 125 extends axially through the valving member 116, from the apex of major conical notch 124 to the apex of minor conical notch 126. Such aperture 125 may be formed during manufacture of the valving member or may simply be formed after the valving member has been positioned within the cannula hub 104 by passing a needle (e.g. the introducer needle 127) or other object therethrough The major conical notch 124 is substantially analogous in configuration to the frusto conical tip of dilator projection 120 and is positioned in relation thereto such that the major conical notch 124 is in alignment with the dilator projection 120 and further such that the dilator projection makes direct contact with the inner surface thereof, even when the valving member 116 is in its "occluding" position.

The radial stresses, compression or biasing of material created by the above-described peripheral axial compression of the valving member causes the inner surface of the major conical notch 124 to seat firmly against and to be guided by the outer camming surface of dilator projection 120. A substantially fluid tight seal is formed therebetween as the valving member alternately moves between its "nonoccluding" and "occluding" positions. Such substantially fluid tight seal prevents blood or other fluids from passing into space 122 wherein such fluids could give rise to undesirable microbial growth or physically interfere with the action of the valving member 116.

Additionally the configuration and peripheral axial compression of the valving member 116 facilitates the functioning of the valving member 116 as it moves between its "occluding" position and its "nonoccluding" position. To wit: the elastomeric material of which the valving member 116 is made is sufficiently elastic to permit the aperture 126 to be stretched or dilated to an open configuration when distally advanced over the frusto conical dilator projection 120. When so positioned, the valving member is in its "nonoccluding" position and free fluid flow is permitted through the cannula lumen. When, however, the distally directed pressure is removed or discontinued, the resilience and/or elasticity of the valving member will cause it to retract or spring back in the proximal direction to a point where the aperture is no longer stretched or dilated by the dilator projection, but rather fully closed and capable of halting fluid flow through the cannula lumen. At such point the valving member is in its "occluding" position.

The changes which take place in configuration of the valving member 116 as it moves between its "occluded" position (FIG. 5) to its "non-occluded" position (FIG. 6) are largely controlled and guided by the outer surface of the dilator projection 120, as well as the axial compression forces applied to the periphery of the valving member 116 which serves to prevent buckling of the valving member 116 which could inadvertently close off, i.e. valve the aperture 130 during use.

An advantage of the preferred embodiment shown in FIG. 5 and 6 is ease of assembly and construction. The proximal segment 108 and distal segment 110 of the cannula hub 104 may initially be formed as separate pieces and subsequently assembled so as to trap the valving member 116 therebetween. In carrying out such assembly process, the peripheral flange portion 117 of valving member 116 is positioned over the proximal rim 112 or leading edge of distal segment 110. The proximal segment 108 is then slidably advanced onto the distal segment 110. Proximal segment 108 and distal segment 110 are forced together to a point where the thickness of the valving member 116 is compressed by approximately twenty percent of its original thickness. Detents or stops 113 are formed on the outer surface of the distal segment. The proximal 108 and distal 110 portions of the hub 104 may then be firmly fixed in relative position by cement, glue or other fixation means.

ii. OPERATION OF THE FIRST EMBODIMENT SHOWN IN FIGS. 1-6

In normal operation, the first preferred embodiment as shown in FIG. 5 will be provided with an additional stylet or introducer needle 127. Such introducer needle 127 is slidably axially disposable within the cannula lumen such that the shaft of the introducer needle 127 will extend through the aperture 126 of the valving member 116. In its fully inserted position the hub of the introducer needle 127 may be partially fitted or advanced into the inner bore 106 of cannula hub 104. The tip of the introducer needle is sharpened or beveled and, when fully inserted, extends beyond the distal end of the flexible cannula 102 so as to facilitate percutaneous insertion of the cannula assembly. After the tip of the cannula sheath 102 has been positioned in a desired blood vessel or other anatomical structure, the introducer needle 127 may be proximally withdrawn from its original fully inserted position within the cannula assembly. The aperture 126 of valving member 116 fits sufficiently snug around the outer shaft of the introducer needle 127 so as to wipe away any adherent blood or other fluid as the needle 127 is proximally withdrawn therefrom.

As the introducer needle 127 is proximally withdrawn and separated from the cannula assembly, the valving member 116 assumes its natural "occluding" position (FIG. 5). Thus, any back flow of blood or other fluids from the cannula will be prevented. Moreover, while the valving member 116 is in such "occluded" position, the inner surface of conical notch 124 is positioned around and in substantially fluid tight contact with the outer surface of dilator projection 120 so that some proximally directed pressure is exerted against the valving member 116 and further such that blood or other fluid will be substantially prevented from leaking into space 122. Such proximally directed pressure may cause the valving member 116 to be biased or toned to its fully occluded, proximal-most position Such proximally directed urging of the valving member 116 may be necessary in cases where the material of which the valving member is made lacks sufficient memory or resiliency to automatically assume its occluding position without exertion of some proximally directed pressure thereon.

A solution administration tube 101, having a male tubing connector 140 formed on an end thereof, or some other object, is then inserted into the inner bore 106 of hub 104 to permit infusion of fluid. As the male tubing connector 140 is distally advanced to its distal-most, fully inserted position, the valving member 116 will be forced thereby in a distal direction. Such distal advancement of the valving member 116 causes the conical notch 124 of valving member 116 to advance over the frusto conical surface of dilator projection 120. When fully distally advanced, the aperture 125 is fully opened or dilated and the body of the valving member is fully displaced in space 122 such that no portion of the valving member obstructs flow of fluid through the lumen 142 of the male tubing connector 140 and/or the lumen 130 of the cannula.

In the event that the male tubing connector 140 becomes disconnected and removed from the hub 104 of cannula assembly 100, the valving member 116 will resiliently and/or elastically return to its original "occluded" position as shown in FIG. 5. Thus, in the event that the male tubing connector 140 is inadvertently pulled out or torn away from the cannula assembly, the valving member 116 will immediately snap back into its "occluded" position to prevent unnecessary back flow and loss of blood or other bodily fluid.

From the above, it will be recognized that due to the specific construction of the valving member 116, dilator projection 120 and axial compression of the peripheral flange 117 of the valving member 116 between the shoulders 112 and 114, the valving member 116 is constrained and guided during its valving cycle to eliminate any inadvertent close off of the aperture 130 as caused by buckling of the valving member 116 and insure proper close off of the aperture 130 when desired.

iii. A SECOND EMBODIMENT SHOWN IN FIGS. 7-11

Depending upon the precise configuration of all working parts of the invention and/or the material of which the valving member is manufactured, it may be necessary to employ a second preferred embodiment of the invention wherein the configuration of the valving member and the surrounding cannula hub are modified so as to prevent any significant deformation of the elastomeric material of the valving member as it moves between its "occluding" and "non-occluding" positions. Such modification may be accomplished by adding a rigidity imparting member or the like to the construction of the valving member. A second preferred embodiment of the invention, incorporating such a rigidifying member, is shown in FIGS. 7 through 11.

Referring specifically to FIGS. 7-11, there is provided a second preferred self-occluding cannula assembly comprising a flexible cannula sheath having a distal end and a proximal end with a cannula hub 204 attached to the proximal end of the tubular sheath. The cannula hub 204 is generally in the configuration of a female Leur connector having an axial inner bore 206 formed therein. The cannula hub 204 is constructed of a proximal hub segment 208 and a distal hub segment 210. The distal hub segment 210 is slidably advancable into the proximal hub segment 208 and subsequently affixed in position such that the proximal rim 212 of the distal hub segment 210 is in direct opposition to an annular shoulder 214 formed about the inner surface of the proximal hub segment 208. By such arrangement, the proximal rim 212 of the distal segment 210 and the annular shoulder 214 of the proximal segment 208 form opposing compression exerting surfaces between which the peripheral flange 217 of valving member 216 may be axially pinched or compressed in the same manner as that described above with reference to the first preferred embodiment shown in FIGS. 2-6.

The valving member 216 of this second preferred embodiment shown in FIGS. 7-11 differs from that of the first preferred embodiment. Specifically, the second preferred valving member 216 comprises a valving member body made of elastomeric or otherwise pliable material having an outer peripheral flange 217 extending therearound. The valving member 216 has a distal end (D) and a proximal end (P), a major conical notch 224 extends axially into the distal end (D) of the mid-portion of the valving member 216. A minor conical notch 226 is formed in the proximal side (P) of the inner mid-region of the valving member 216 such that the apex of the minor conical notch 226 directly opposes or joins with the apex or innermost extent of the major conical notch 224. Thus, a pin hole or substantially self-sealing aperture 225 may extend axially through the mid-region of the valving member 226, joining the apex of the minor conical notch 226 with the apex of innermost extent of the major conical notch 224. Such aperture may be formed during the manufacture of the valving member or may simply be formed after the valving member has been positioned within the cannula hub 104 by passing a needle (e.g. the introducer needle 127) or other object therethrough.

As in the first preferred embodiment described above, the major conical notch 224 of the valving member 216 is substantially analogous in configuration to the frusto conical tip of the dilator projection 220 formed within the cannula hub 204. Additionally, an annular rib or "O" ring 300 is formed about the inner surface of the major conical notch 224. Such annular rib or "O" ring 300 is sized and configured to seat within and/or snap fit into a corresponding annular groove 302 formed in the outer surface of the conical dilator projection 220. The annular rib or "O" ring 300 is positioned such that when the valving member 216 is in its "non-occluding" position, the annular rib or "O" ring 300 of the valving member 216 will seat into the annular groove 302, thereby enhancing the tightness and fluid retaining capacity of the seal formed between the inner surface of the valving member 216 and the outer surface of the conical dilator projection 220.

Additionally, to further facilitate controlled manipulation and movement of the valving member 216 in response to distally directed pressure exerted by insertion of a male connector 240 into the inner bore 206 of the cannula hub, there is provided a proximal extension 320 extending proximally from the mid-region of the valving member 216. Such proximal extension 320 comprises a generally cylindrical extension of the valving member body having an axial inner bore 322 and a peripheral lip or flange 324 extending annularly around the proximal end thereof.

An annular groove or space S is thereby formed between the distal surface of peripheral flange 324 and the proximal surface of major flange 217. A rigid reinforcement ring 330 is positionable fully or partially within space S so as to form a rigid collar about the proximal extension 320 of the valving member 216. Such rigid ring 330 may be formed of plastic, metal or other rigid material(s). Preferably, the rigid ring 330 is positioned on the valving member 216 after the elastomeric or pliable valving member 216 has been molded or otherwise formed. It is possible, however, that the rigid ring 330 may be molded in place or otherwise pre-set in its desired position during manufacture of the valving member 216.

iv. OPERATION OF THE SECOND EMBODIMENT SHOWN IN FIGS. 7-11

The manner in which the second preferred embodiment of the invention operates may be appreciated by referring to FIGS. 10 and 11.

In normal operation, the second preferred embodiment as shown in FIG. 10, will be provided with an additional stylet or introducer needle 227. Such introducer needle 227 is slidably axially disposable within the cannula lumen such that the shaft of the introducer needle 227 will extend through the aperture 225 of the valving member 216. In its fully inserted position, the hub of the introducer needle 227 may be partially fitted or advanced into the inner bore 206 of the cannula hub 204. The tip of the introducer needle is sharpened or beveled, and when fully inserted, extends beyond the distal end of the flexible cannula (not shown) so as facilitate percutaneous insertion of the cannula assembly.

After the tip of the cannula sheath 102 has been positioned in a desired blood vessel or other anatomical structure, the introducer needle 227 may be proximally withdrawn from its fully inserted position within the cannula assembly. The aperture 226 of valving member 216 fits sufficiently snug around the outer shaft of the introducer needle 227 so as to wipe away any adherent blood or other fluid as the needle 227 is proximally withdrawn therefrom.

As the introducer needle 227 is proximally withdrawn and separated from the cannula assembly, the valving member 216 assumes its natural "occluding" position (FIG. 10) wherein the central aperture 226 is fully closed so as to prevent any backflow of blood or other fluids from the cannula lumen. Moreover, while the valving member 216 is in such "occluded" position, the inner surface of the conical notch 224 is in substantially fluid tight contact with the outer surface of the conical dilator projection 220 so as to prevent leakage of blood or other fluids into space 222. Additionally, the contact between the inner surface of the conical notch 224 and the outer surface of the conical dilator projection 220, in accordance with the frusto conical shape of the dilator projection 220, may exert some degree of proximally directed pressure on the valving member 216 so as to urge it to remain in its occluding position.

Additionally, as shown in FIG. 10 the annular rib or "O" ring 300 is positioned near and in contact with the frustum of the dilator projection 220. This contact further enhances the fluid tight seal formed between the valving member 217 and the dilator projection 220.

Thus, as shown in FIG. 10, the valving member 216 rests in its normal "occluding" position While resting in such "occluding" position, some degree of proximally directed pressure may be created by interaction of the frusto conical dilator projection 220 and the valving member 216. In a preferred embodiment, such proximally directed pressure will urge the valving member 216 to be biased or toned to its fully occluded, proximal-most position. Such exertion of pressure is not, however, necessary in all embodiments of the invention, and, indeed, the valving member 216 may be endowed with sufficient memory or resiliency to automatically return to its "occluding" position from its "non-occluding" position when the male connector is removed from the cannula hub 204.

In normal operation, after the cannula has been inserted and the introducer needle 227 removed, a male connector 240 will be inserted into the female bore 206 of the cannula hub 204. As the male tubing connector 240 is distally advanced to its distal-most fully inserted position, the valving member 216 will be forced thereby in a distal direction. The rigid ring 330 positioned about the proximal extension of valving member 216 will serve to enhance and direct the compression of the valving member 216 over frusto conical dilator projection 220.

Accordingly, the distal advancement of the valving member 216 causes the conical notch 224 of valving member 216 to advance over the frusto conical surface of dilator projection 220. Fully distally advanced, the aperture 225 is fully opened or dilated and the body of the valving member 216 is displaced into space 222. Additionally, the annular rib or "O" ring 300 will firmly seat within annular groove 302. Such seating of the annular rib or "O" ring 300 within groove 302 will enhance the tightness of the field of the valving member 216 and the frusto conical dilator projection 220 thereby preventing leakage of blood or other fluids into space 222.

When fully distally advanced to its "non-occluding" position, no portion of the valving member 216 will obstruct flow of fluid through the lumen 242 of the male tubing connector and/or the lumen 230 of the cannula. Accordingly, free infusion and/or withdrawal of fluid is permitted.

In the event that the male tubing connector 240 becomes disconnected and removed from the hub 204 of the cannula assembly, the valving member 216 will resiliently and/or elastically return to its original "occluded" position as shown in FIG. 10 Thus, in the event that the male tubing connector is inadvertently pulled out or torn away from the cannula assembly, the valving member 216 will immediately snap back into its "occluding" position to prevent unnecessary backflow and loss of blood or other bodily fluid.

From the above, it will be appreciated that due to the specific construction of the valving member 216, dilator projection 220 and the axial compression of the peripheral flange 217 of the valving member 216, between shoulder 212 and 214, the valving member 216 is constrained and guided during its valving cycle to eliminate any inadvertent close-off of the aperture 225 as caused by buckling of the valving member 216 and to insure proper close-off of the aperture 225 when desired. Additionally, the provision of the rigid ring 330 will serve to control and direct the distally directed pressure exerted by the male tubing connector 240. Such will insure that the mid-portion of the valving member 216 will fully advance over frusto conical dilator projection 220 so as to assume the desired "non-obstructing" configuration shown in FIG. 11.

Although the invention has been described herein with reference to a presently preferred embodiments thereof, it will be appreciated that various additions, deletions modifications and alterations may be made to such preferred embodiments without departing from the spirit and scope of the invention. Accordingly, it is intended that any and all such additions, deletions alterations and modifications be included within the scope of the following claims and the equivalents thereof.

What is claimed is:

1. A self-occluding cannula assembly comprising:
   a generally tubular cannula sheath having a proximal end, a distal end and an inner lumen extending axially therethrough;
   a connecting hub formed on the proximal end of said cannula sheath, said connecting hub having an axial bore formed therein, said axial bore being fluidly consistent with the inner lumen of said cannula sheath; and
   an occluding means comprising:
   a generally frusto conical dilator projection formed within the bore of said connecting hub;
   an elastomeric valving member having a peripheral portion and a mid-portion,
   said elastomeric valving member being positioned transversely within the bore of said connecting hub, proximal to said dilator projection, with the peripheral portion thereof being axially compressed so as to cause the exertion of radially inward pressure toward the mid-portion thereof; and
   an elastically openable and closable aperture extending axially through the mid-portion of said valving member;
   said peripherally compressed valving member being alternately movable between an "occluding" position wherein said openable and closable aperture remains closed so as to substantially preclude fluid flow through said cannula lumen; and a "non-occluding" position wherein the mid-portion of said valving member is advanced over at least a portion of said dilator projection such that the dilator projection exerts sufficient pressure against said valving member to cause said openable and closable aperture to assume an open configuration thereby allowing fluid flow through said cannula lumen; and
   said valving member, when in said "non-occluding" position being sufficiently resilient to automatically return to said "occluding" position when said distally directed pressure is removed therefrom.

2. The self-occluding cannula assembly of claim 1 further comprising:
   an introducer needle slidably axially disposed within said cannula lumen,
   said introducer needle comprising an elongate needle shaft having a sharpened distal tip;
   said sharpened distal tip extending beyond the distal end of said flexible cannula sheath so as to facilitate percutaneous insertion of said cannula sheath.

3. The self-occluding cannula assembly of claim 2 wherein said introducer needle extends through the openable and closable aperture of said valving member.

4. The self-occluding cannula assembly of claim 3 wherein the openable and closable aperture of the valving member, when in its "occluding" position fits snugly about said introducer needle so as to wipe adherent fluid from the introducer needle as said introducer needle is proximally withdrawn from the cannula assembly.

5. The self-occluding cannula assembly of claim 4 wherein said introducer needle comprises a generally hollow needle having an open axially extending inner lumen through which fluid may flow upon insertion of the distal tip of the needle into a fluid filled anatomical structure.

6. The self-occluding cannula assembly of claim 1 wherein at least a portion of said cannula hub comprises a female tubing connector having an inner bore into which a correspondingly shaped male tubing connector may be inserted.

7. Self-occluding cannula assembly of claim 1 wherein said elastomeric valving member comprises:
   a disk-like body positioned transversely within the bore of said connecting hub and having a distal side and a proximal side, at least one major conical notch being formed within the distal side of said valving member, and further wherein said aperture extends into said major conical notch such that distally directed advancement of said valving member will cause said conical notch to ride over said frusto conical dilator projection thereby allowing said frusto conical dilator projection to exert said pressure against said valving member to cause said openable and closable aperture to assume its open configuration 8. Self-occluding cannula assembly of claim 7 wherein said valving member further comprises a generally cylindrical proximal extension extending therefrom with a rigid ring formed therearound, said rigid ring on said proximal extension being operative to confine and direct distally directed pressure against the mid-portion of said valving member.

9. The self-occluding cannula assembly of claim 1 wherein said valving assembly further comprises an annular rib formed within said conical notch and further wherein said frusto conical dilator projection is provided with an annular groove on the outer surface thereof, the annular rim within the conical notch of said valving member and annular groove on the outer surface of said frusto conical dilator projection being correspondingly sized, shaped and configured so that upon positioning of said valving member in a given position relative to said frusto conical dilator projection, said annular rib will seat within said annular groove.

10. The self-occluding cannula assembly of claim 9 wherein said annular rib comprises an O ring.

11. The self-occluding cannula of claim 8 wherein said rigid ring comprises a ring of plastic.

* * * * *